US009278184B2

(12) United States Patent
Sofranko

(10) Patent No.: US 9,278,184 B2
(45) Date of Patent: Mar. 8, 2016

(54) PRESSURE SUPPORT SYSTEM WITH INDUCTIVE TUBING

(75) Inventor: Richard Andrew Sofranko, Finleyville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 709 days.

(21) Appl. No.: 13/503,470

(22) PCT Filed: Sep. 28, 2010

(86) PCT No.: PCT/IB2010/054368
§ 371 (c)(1),
(2), (4) Date: Apr. 23, 2012

(87) PCT Pub. No.: WO2011/051837
PCT Pub. Date: May 5, 2011

(65) Prior Publication Data
US 2012/0204874 A1    Aug. 16, 2012

Related U.S. Application Data

(60) Provisional application No. 61/255,651, filed on Oct. 28, 2009.

(51) Int. Cl.
*A61M 16/06* (2006.01)
*A61M 16/00* (2006.01)
(Continued)

(52) U.S. Cl.
CPC ............. *A61M 16/06* (2013.01); *A61M 16/00* (2013.01); *A61M 16/0816* (2013.01); A61M 16/0875 (2013.01); *A61M 16/1095* (2014.02); *A61M 16/161* (2014.02); *A61M 16/0066* (2013.01); *A61M 2016/0027* (2013.01); *A61M 2016/0033* (2013.01); *A61M 2039/1033* (2013.01); *A61M 2205/3324* (2013.01); *A61M 2205/3368* (2013.01); *A61M 2205/3375* (2013.01); *A61M 2205/3561* (2013.01);
(Continued)

(58) Field of Classification Search
CPC .............. A61M 16/08; A61M 16/161; A61M 16/1095; A61M 39/1055; A61M 16/00; A61M 16/0051; A61M 16/0069; A61M 16/06; A61M 16/0816; A61M 16/0875; A61M 15/0003; G06K 7/10178; A61N 5/0603; A61N 5/06; A61B 5/05; A61B 5/083; A61B 5/14539; B32B 27/04; B32B 27/12; B32B 5/02; G01N 1/22; G01N 31/00; G01N 33/497
USPC ............. 128/200.24, 204.22, 205.23, 204.18, 128/204.21, 204.23, 204.17, 911, 912, 128/203.12, 203.16; 600/529, 532, 538, 600/300
See application file for complete search history.

(56) References Cited

U.S. PATENT DOCUMENTS 5,630,836 A    5/1997 Prem
5,815,383 A    9/1998 Lei
(Continued)

FOREIGN PATENT DOCUMENTS

CN    1881275 A    12/2006
CN    101541367 A    9/2009
(Continued)

*Primary Examiner* — Annette Dixon
(74) *Attorney, Agent, or Firm* — Michael W. Haas

(57) ABSTRACT

A pressure support system includes a gas flow generating system a patient interface device, and a tubing. The gas flow generating system includes a gas source, a controller, and a first inductive coil. The patient interface device includes a second inductive coil and an input element. The tubing is disposed between the flow generating system and the patient interface device to carry a flow of gas from the gas source to the patient interface device. The tubing includes a third inductive coil structured to transmit power and/or a signal between the first inductive coil of the pressure support system controller and the second inductive coil of the patient interface device.

15 Claims, 4 Drawing Sheets

(51) Int. Cl.
*A61M 16/08* (2006.01)
*A61M 16/10* (2006.01)
*A61M 16/16* (2006.01)
*A61M 39/10* (2006.01)

(52) U.S. Cl.
CPC .............. *A61M 2205/3569* (2013.01); *A61M 2205/3576* (2013.01); *A61M 2205/8243* (2013.01); *A61M 2230/04* (2013.01); *A61M 2230/10* (2013.01); *A61M 2230/60* (2013.01); *A61M 2230/62* (2013.01); *A61M 2230/63* (2013.01)

(56) References Cited

U.S. PATENT DOCUMENTS

| | | | |
|---|---|---|---|
| 5,880,942 A | 3/1999 | Leu | |
| 6,058,330 A | 5/2000 | Borza | |
| 6,240,921 B1 * | 6/2001 | Brydon et al. | 128/205.23 |
| 6,323,728 B1 | 11/2001 | Schmitt-Landsiedel | |
| 6,357,438 B1 | 3/2002 | Hansen | |
| 7,297,120 B2 | 11/2007 | Tsukashima | |
| 7,544,204 B2 * | 6/2009 | Krespi et al. | 607/88 |
| 2002/0023649 A1 | 2/2002 | Gunaratnam | |
| 2004/0163648 A1 | 8/2004 | Burton | |
| 2004/0182392 A1 * | 9/2004 | Gerder et al. | 128/204.22 |
| 2005/0016540 A1 | 1/2005 | Jumpertz | |
| 2008/0078388 A1 | 4/2008 | Vandine | |
| 2008/0173308 A1 | 7/2008 | Schermeier | |

FOREIGN PATENT DOCUMENTS

| | | |
|---|---|---|
| EP | 0585788 A1 | 3/1994 |
| EP | 1127583 A2 | 8/2001 |
| EP | 2169816 A1 | 3/2010 |
| WO | WO2005002655 A1 | 1/2005 |
| WO | WO2008091164 A1 | 7/2008 |

* cited by examiner

PRESSURE SUPPORT SYSTEM WITH INDUCTIVE TUBING

CROSS-REFERENCE TO RELATED APPLICATIONS

This patent application claims the priority benefit under 35 U.S.C. §371 of international patent application no. PCT/IB2010/054368, filed Sep. 28, 2010, which claims the priority benefit under 35 U.S.C. §119(e) of U.S. Provisional Application No. 61/255,651 filed on Oct. 28, 2009, the contents of which are herein incorporated by reference.

BACKGROUND OF THE INVENTION

1. Field of the Disclosure

The present invention pertains to pressure support systems, and, in particular, to such pressure support systems employing a controller, breathing tube, an interface device, and a method of inductively transmitting power or signals between the patient interface device and the controller.

2. Description of the Related Art

Referring to FIG. 1, a conventional pressure support system 50 includes a gas flow generator 52, such as a blower, and is typically used as a continuous positive airway pressure (CPAP) or bi-level pressure support device. System 50 receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of patient 54 at relatively higher and lower pressures, i.e., generally equal to or above ambient atmospheric pressure. Gas flow generator 52 is capable of providing a flow of breathing gas ranging in pressure from about 3-30 cmH$_2$O. The pressurized flow of breathing gas, generally indicated by arrow D from gas flow generator 52, is delivered via a delivery conduit 56 to a breathing mask or patient interface 58 of any known construction, which is typically worn by or otherwise attached to patient 54 to communicate the flow of breathing gas to the airway of patient 54. Delivery conduit 56 also known in the art as a patient circuit.

Pressure support system 50 is what is known as a single-limb system, meaning that the patient circuit includes only one delivery conduit 56 connecting patient 54 to pressure support system 50. As such, an exhaust vent 57 is provided in delivery conduit 56 for venting exhaled gasses from the system as indicated by arrow E. Exhaust vent 57 can be provided at other locations in addition to or instead of in delivery conduit 56, such as in patient interface device 58. Exhaust vent 57 can have a wide variety of configurations depending on the desired manner in which gas is to be vented from pressure support system 50.

Pressure support system 50 includes a pressure controller in the form of valve 60 provided in delivery conduit 56. Valve 60 controls the pressure of the flow of breathing gas from flow generator 52 delivered to patient 54. Flow generator 52 and valve 60 are collectively referred to a pressure generating system because they act in concert to control the pressure and/or flow of gas delivered to patient 54. However, other techniques for controlling the pressure of the gas delivered to patient 54, such as varying the blower speed of flow generator 52, either alone or in combination with a pressure control valve, can be employed. Thus, valve 60 is optional depending on the technique used to control the pressure of the flow of breathing gas delivered to patient 54. If valve 60 is eliminated, the pressure generating system corresponds to flow generator 52 alone, and the pressure of gas in the patient circuit is controlled, for example, by controlling the motor speed of flow generator 52.

Pressure support system 50 further includes flow sensor 62 that measures the flow of the breathing gas within delivery conduit 56. Flow sensor 62 is interposed in line with delivery conduit 56, most preferably downstream of valve 60. Flow sensor 62 generates a flow signal that is provided to controller 64 and is used by controller 64 to determine the flow of gas at patient 54. Of course, other techniques for measuring the respiratory flow of patient 54 can be employed, such as measuring the flow directly at patient 54 or at other locations along delivery conduit 56 and communicating the measured flow by direct electrical connection between a flow sensor (not shown) and controller 64, measuring patient flow based on the operation of flow generator 52, and measuring patient flow using a flow sensor (not shown) upstream of valve 60.

Pressure support system 50 also includes pressure sensor 68 operatively coupled to controller 64 that detects the pressure of the gas at patient 54. Pressure sensor 68 is in fluid communication with patient interface 58 via delivery conduit 56. The pressure at patient 54 is estimated based on the known pressure drop that occurs in delivery conduit 56. Alternatively, the patient pressure can be measured directly at patient interface 58 using a pressure sensor (not shown) incorporated therein and communicating the measured pressure by direct electrical connection (not shown) between such pressure sensor (not shown) and controller 64.

Controller 64 may be, for example, a microprocessor, a microcontroller or some other suitable processor or processing device, that includes or is operatively coupled to a memory (not shown) that provides a storage medium for data and software executable by controller 64 for controlling the operation of pressure support system 50.

Input/output device 66 is provided for setting various parameters used by pressure support system 50, as well as for displaying and outputting information and data to a user, such as a clinician or caregiver.

Pressure support system 50 essentially functions as a CPAP pressure support system, and, therefore, includes all of the capabilities necessary in such systems in order to provide appropriate CPAP pressure levels to patient 54. This includes receiving the necessary parameters, via input commands, signals, instructions or other information, for providing appropriate CPAP pressure, such as maximum and minimum CPAP pressure settings. Other pressure support methodologies, include but are not limited to, BiPAP AutoSV, AVAPS, Auto CPAP, and BiPAP Auto.

It is known to provide a sensor at patient interface 58. See, e.g., U.S. patent application Ser. No. 10/777,572 to Burton (publication No. 2004/0163648). However, there is a challenge in transmitting information collected by such a sensor to controller 64 without providing cumbersome hardwired connections between these two elements. Wireless connections also present a problem in that it is desirable to minimize the mass or bulk contained on patient interface 58, which it typically worn by the user for extended periods of time. As a result, providing batteries, transmitters, and other items typically used in a wireless communication system at or on patient interface 58 is not appealing.

SUMMARY OF THE INVENTION

Accordingly, it is an object of the present invention to provide a pressure support system that overcomes the shortcomings of conventional pressure support system. This object is achieved according to one embodiment of the present invention by providing a pressure support system comprising a gas flow generating system, a patient interface device, and a tubing. The gas flow generating system includes a gas source, a controller, and a first inductive coil coupled to the controller. The patient interface device includes an input element operatively coupled to the patient interface device, and a second inductive coil operatively coupled to the input element and disposed on the patient interface device. The tubing is disposed between the pressure support system controller and the patient interface device and is structured to carry a flow of air or gas from the gas source to the patient interface device. The tubing includes a third inductive coil coupled thereto and structured to transmit power or a signal between the first inductive coil of the pressure support system controller and the second inductive coil of the patient interface device.

It is a still further object of the present invention to provide a patient interface device that overcomes the problems associated with using conventional patient interface devices. This object is achieved by providing a patient interface device that includes a frame, a cushion coupled to the frame, a connector portion rotatably coupled to the frame, an input element operatively coupled to the frame, the cushion, the connector portion, or any combination thereof, and a first inductive coil operatively coupled to the connector portion and in electrical communication with the input element. The first inductive coil is structured to transmit power, a signal, or both between the first inductive coil and a second inductive coil It is yet another object of the present invention to provide a method of method of providing a flow of gas to a patient that does not suffer from the disadvantages associated with conventional methods. This object is achieved by providing a method that includes employing a patient interface device comprising a first inductive coil and an input element; providing a gas flow from a gas flow generating system having a second inductive coil; communicating a flow of gas to the patient interface device from the gas flow generating system via a tubing coupled between the patient interface device from the gas flow generating system, wherein the tubing includes a third inductive coil; and transmitting power, a signal, or both between the input element and a controller in the gas flow generating system through an inductive coupled between first and the third inductive coils and between the second and the third inductive coils.

These and other needs, features, and characteristics of the present invention, as well as methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF EXEMPLARY EMBODIMENTS

As employed herein, the term "number" shall mean one or an integer greater than one (i.e., a plurality). As employed herein, the term "processor" means a programmable analog and/or digital device that can store, retrieve, and process data; a computer; a workstation; a personal computer; a microprocessor; a microcontroller; a microcomputer; a central processing unit; a mainframe computer; a mini-computer; a server; a networked processor; a field programmable gate array; a controller; or any suitable processing device or apparatus.

As employed herein, the term "patient interface device" means a device that communicates a flow of gas with an airway of the user, such as a nasal mask, an oral mask, a nasal/oral mask, a nasal pillow, nasal cannula, a tracheal tube, an endotracheal tube, any other device or apparatus that provides a suitable air or gas flow communicating function.

As employed herein, the term "sensor" means a sensing device or apparatus structured to sense, for example and without limitation, pressure, flow, heat, vibration, g-force, electromyography (EMG), electroencephalography (EEG), electrocardiography (ECG or EKG), pH, sound and body position. As employed herein, the term "control" means a controlling device or apparatus structured to control, such as, for example and without limitation, a valve; an exhaust valve; another mechanical device; and other combinations of sensors, circuitry and software. As used herein, the phrase "input element" refers to a sensor (as defined above), a control (as defined above), or any combination thereof.

As employed herein, the term "tubing" means a conduit; a delivery conduit; a tube, pipe, passage, or channel through which air or gas flows; a structure providing an air or gas flow communicating function; and any other structure that connects a source of pressurized breathing air or gas to a patient or patient interface device.

As employed herein, the term "inductive" means a circuit, device, apparatus or tubing possessing inductance. As employed herein, the statement that two or more parts are "coupled" together means that the parts are joined together either directly or joined through one or more intermediate parts. As employed herein, the statements that two or more electrical components are "electrically coupled" together or are in "electrical communication" mean that the electrical components are directly electrically connected together or are electrically connected together through one or more intermediate electrical components or conductors.

Figure 1:
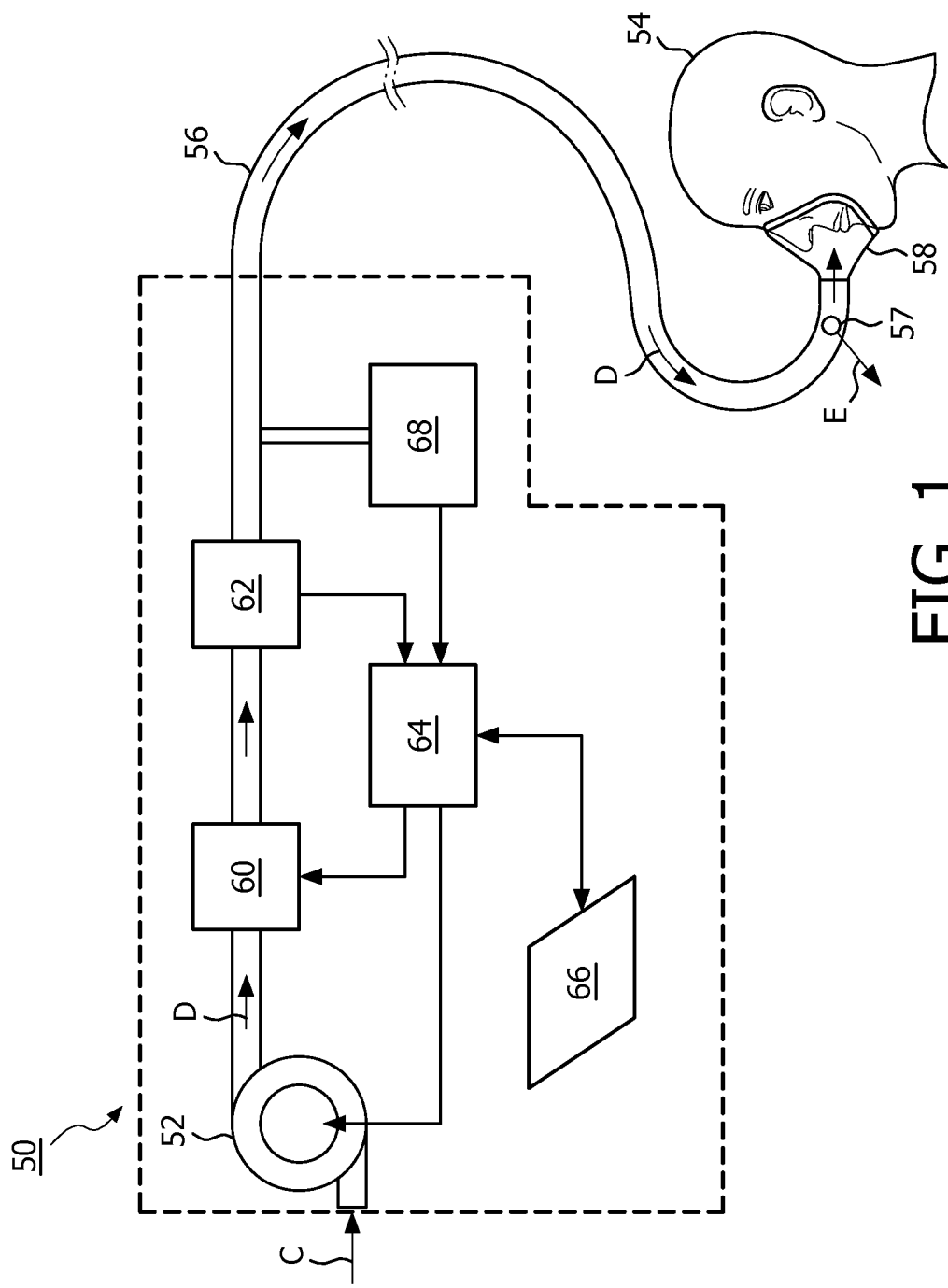
FIG. 1 is a block diagram in schematic form of a pressure support system.
Figure 2A:
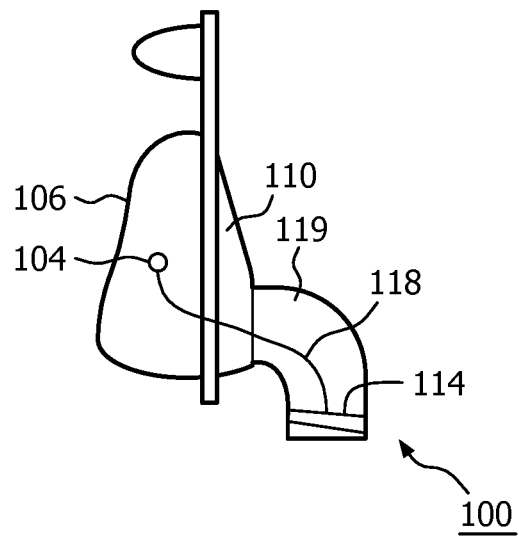
FIGS. 2A and 2B are elevation views of patient interface devices, such as masks, in accordance with embodiments of the invention.
Figure 2B:
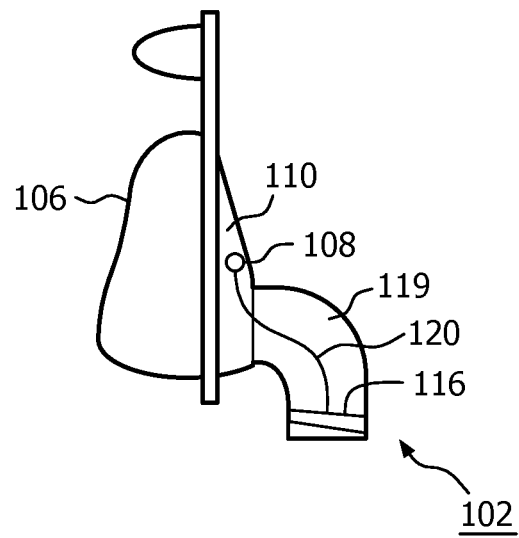

Referring to FIGS. 2A and 2B, example patient interface devices 100 and 102, respectively, are shown. In FIG. 2A, an input element 104, such as a sensor or control, is coupled to a cushion 106 in patient interface device 100. In FIG. 2B, input element 108 is coupled to a frame 110 in to patient interface device 102. The physical phenomena measured by input element 104,108 can include, for example and without limitation, pressure, flow, heat, vibration, g-force, electromyography (EMG), electroencephalography (EEG), electrocardiography (ECG or EKG), pH, sound and body position. Input elements 104,108 can have local electrical components (not shown) operatively associated therewith or, conversely, such electrical components can be located at a separate pressure support system controller (e.g., without limitation, control unit 112, as shown in FIG. 3).

Although input elements 104,108 are shown, it will be appreciated that any suitable number of input elements (sensors, controls, or both) can be employed as is discussed below in connection with FIG. 5. As shown in FIGS. 2A and 2B, each input element 104,108 is in electrical communication with respective inductive coils 114,116 via electrical conductors 118,120.

As shown in FIGS. 2A and 2B, patient interface device 100 and 102 includes a connector portion 119 coupled to the frame. In an exemplary embodiment, input element 104, 108 can also be provided on connector portion 119 in place of or in addition to the placements shown in FIGS. 2A and 2B. In an further embodiment, connector portion is rotatably coupled to frame 110.

Figure 3:
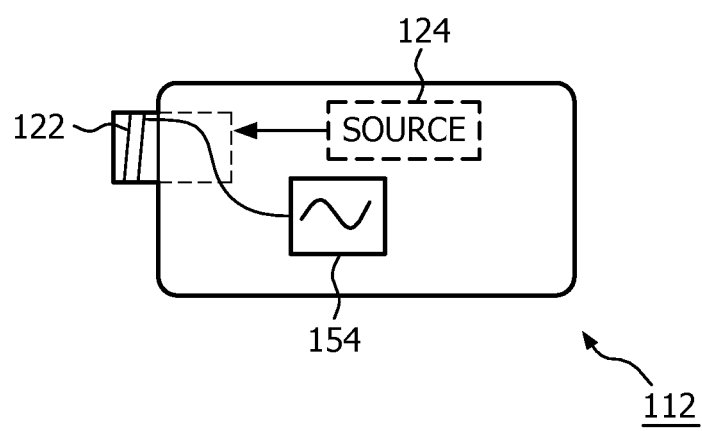
FIG. 3 is an elevation view of a pressure support system controller in accordance with another embodiment of the invention.

As shown in FIG. 3, gas flow generating system 112 includes an inductive coil 122, a gas source 124 (e.g., without limitation, a gas flow generator such as blower), and a controller (154) as will be described below in connection with FIG. 5.

Figure 4:
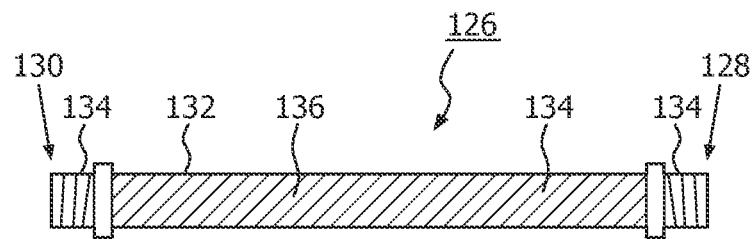
FIG. 4 is an elevation view of inductive tubing in accordance with another embodiment of the invention.

FIG. 4 shows an inductive tubing 126 that is connected between patient interface device (100, 102) and gas flow generating system 112. Inductive tubing 126 including a first end 128, an opposite second end 130, and an elongated tube 132 disposed between first end 128 and opposite second end 130. Typically, first end 128 or second end 130 is coupled to connector portion 119 and the remaining other of first end 128 and second end 130 is coupled to an outlet of pressure generating system 144. An inductive coil 134, or a plurality of inductive coils, is wound about first end 128, elongated tube 132, and opposite second end 130. The present invention contemplates that elongated tube 132 is a conduit having a wall 136 (e.g., cylindrical).

Inductive coil 134 can be attached or otherwise coupled to the tubing using an suitable technique, for example and without limitation, embedded in, adhered to, wrapped about or otherwise held against tube wall 136. It will be appreciated that the inductive coil or coils can also or alternatively be embedded in or suitably adhered to tubing connectors (e.g., without limitation, tubing connectors 156,158 of FIG. 5), tubing cuffs (e.g., tubing ends 128,130) and/or tubing swivels (e.g., without limitation, swivel connector 170 of FIG. 6).

Figure 5:
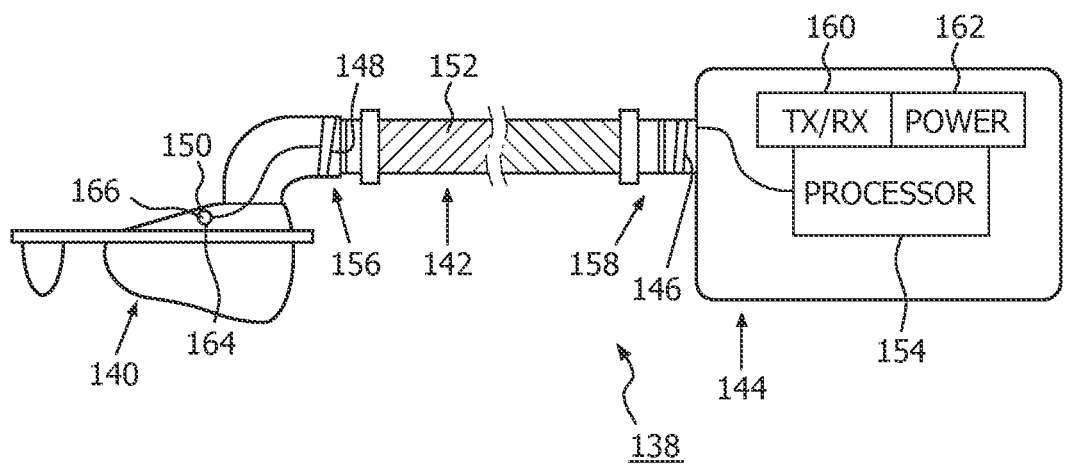
FIG. 5 is an elevation view of a ventilator system including a patient interface device, inductive tubing and a pressure support system controller in accordance with another embodiment of the invention.

Referring to FIG. 5, a pressure support system 138 includes a patient interface device 140, inductive tubing 142, and gas flow generating system 144, which can be the same as or similar to example gas flow generating system 112 of FIG. 3. Gas flow generating system 144 includes an inductive coil 146, and a gas source (not shown, but see gas source 124 of FIG. 3). Patient interface device 140 includes an inductive coil 148 and at least one input element 150. Inductive tubing 142 is disposed between gas flow generating system 144 and patient interface device 140. Similar to inductive tubing 126 of FIG. 4, inductive tubing 142 is structured to provide a flow of gas from the gas source gas flow generating system 144 to patient interface device 140. Similar to tubing 126 (FIG. 4), tubing 142 includes an inductive coil 152 coupled thereto and structured to transmit power and/or a signal between inductive coil 146 of gas flow generating system 144 and inductive coil 148 of patient interface device 140.

Input element 150 and processor component 154 of pressure support system controller 144 are in electrical communication with inductive coils 148 and 146, respectively. For example, inductive coils 148,146 include a number of turns of a suitable conductor around corresponding tubing connectors 156,158, respectively. For example, each adjacent pair of inductive coils 148,152 and 152,146 is in suitably close proximity with no direct electrical connection therebetween. At, for example, controller end (to the right with respect to FIG. 5) or at input element end (to the left with respect to FIG. 5), and in electrical communication with respective inductive coils 146,148, there can be one or more of a receiver, a transmitter, a transceiver and a power source.

For example and without limitation, processor component 154 includes transceiver (TX/RX) 160 and power source 162, and number of sensors or controls 150 includes transceiver 164 and sensor power source 166. As will be explained, power source 162 can transmit power through number of inductive coils 152 between inductive coil 146 of pressure support system controller 144 and inductive coil 148 of patient interface device 140 to sensor power source 166 (e.g., for example and without limitation, to, in turn power number of sensors or controls 150). Also, transceiver 160 can transmit or receive a number of signals through number of inductive coils 152 between inductive coil 146 of pressure support system controller 144 and inductive coil 148 of patient interface device 140 to or from transceiver 164 of patient interface device 140. Other non-limiting exemplary configurations for the pressure support system, according to the principles of the present invention are discussed below.

EXAMPLE 1

In one embodiment, input element 150 is a sensor in electrical communication with inductive coil 148. Power source 162 transmits power to such sensor through an inductive coupling between inductive coil 146 and inductive coil 152, and between number of inductive coil 152 and inductive coil 148. A transmitter of transceiver 164 transmits signals to a receiver (RX) of controller transceiver 160 through inductive coupling between inductive coil 148 and inductive coil 152, and between inductive coil 152 and inductive coil 146.

EXAMPLE 2

Input element 150 is a control in electrical communication with inductive coil 148. Power source 162 transmits power to such control through an inductive coupling between inductive coil 146 and inductive coil 152, and between inductive coil 152 and inductive coil 148. A receiver of control transceiver 164 receives a number of signals from transmitter (TX) of controller transceiver 160 through inductive coupling between inductive coil 146 and inductive coil 152, and between inductive coil 152 and inductive coil 148.

EXAMPLE 3

Input element 150 is a combination of a sensor and a control both of which are in electrical communication with inductive coil 148. Power source 162 transmits power to such sensor and control through an inductive coupling between inductive coil 146 and inductive coil 152, and between inductive coil 152 and inductive coil 148. A receiver of control transceiver 164 receives signals from transmitter of controller transceiver 160 through inductive coupling between inductive coil 146 and inductive coil 152, and between inductive coil 152 and inductive coil 148. A transmitter of transceiver 164 transmits signals to a receiver of controller transceiver 160 through an inductive coupling between inductive coil 148 and inductive coil 152, and between inductive coil 152 and inductive coil 146.

EXAMPLE 4

Input element 150 is in electrical communication with inductive coil 148. The input element receives a control signal having one of a plurality of different states from transmitter of controller transceiver 160 through an inductive coupling between inductive coil 146 and inductive coil 152, and between inductive coil 152 and inductive coil 148. For example, such input element can be structured to respond differently to different states (e.g., without limitation, different frequencies; different signal magnitudes) of control signal. For example, a pressure support system, such as 138, can switch therapy modes to address a change in the patient's air delivery needs. This could be a variation in the pressure level delivered or a variation to the synchrony of the air delivery wave in comparison to the patient's breathing pattern. Variations in the humidity of the patient-exhaled air sensed by a humidity sensor of patient interface device 140 could, for instance, trigger an adjustment to a humidity control of pressure control system 138. Conversely, if a moisture sensor positioned within a mask of patient interface device 140 sensed condensate, then system humidity could advantageously be reduced to eliminate more condensate.

EXAMPLE 5

In this example, the present invention contemplates that inductive coil 152 is structured to generate heat to warm the flow of gas passing through inductive tubing 142. Power source 162 transmits power to inductive coil 152 through an inductive coupling between inductive coil 146 and number of inductive coils 152. The inductive tubing can be made from any material that facilitates the transmission of heat from inductive coil 152 to the interior of the tube.

EXAMPLE 6

The example inductive tubing 126 (FIG. 4) or 142 (FIG. 5) provides a suitable inductive link or inductive element that permits the transmission of energy and/or data across an air gap (e.g., without limitation, from and/or to inductive coils 146 and/or 148). For example, power transmitted to patient interface device 140 can power elements (e.g., without limitation, sensors, controls, etc.) thereof. Such power can, for example and without limitation, have a fluctuation or periodicity to it (e.g., the same as or similar to a sine wave). This variation can be suitably configured to have no impact to the power provided, but can be configured, for example and without limitation, as a controlling signal (e.g., without limitation, such as a carrier wave). For instance, a sensor or a control at patient interface device 140 could be configured to behave in different manners depending on the state (e.g., without limitation, frequency) of the controlling signal.

For example, as shown in FIG. 5, controller transceiver 160 and controller power source 162 respectively can convey a number of signals from number of sensors or controls 150 and power thereto. Also, controller transceiver 160 can convey a number of signals to number of sensors or controls 150. Non-limiting examples of transceivers, power sources and power supplies are disclosed by U.S. Pat. Nos. 5,630,836 and 6,058,330, which are incorporated by reference herein.

When patient interface device 140 and example pressure support system controller 144 are coupled to example inductive tubing 142, a power and data transmission link is formed which enables advanced sensing/control capabilities. A byproduct of such advanced capabilities is advanced device control for improved therapy (e.g., without limitation, having a better physiologic signal (e.g., without limitation, a signal measured on a mask; a signal measured at a patient interface device) permits a therapy device to better respond to physiologic needs). Most known ventilators do not provide this function, since patient response is typically measured back at therapy device, controller or on non-patient side of conventional tubing. If a sensor is provided on a mask, then it is believed that its sensor signal is communicated back to therapy device, controller or on non-patient side of tubing by a direct electrical connection.

EXAMPLE 7

Figure 6:
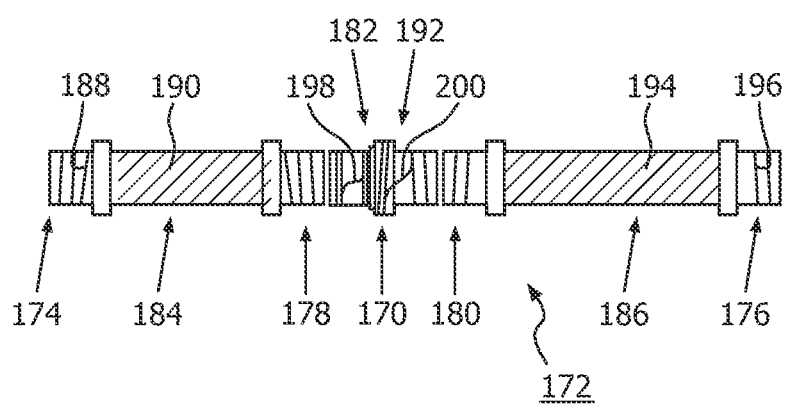
FIG. 6 is an elevation view of inductive tubing including a swivel connector in accordance with another embodiment of the invention.

FIG. 6 shows an example of a swivel connector 170 as part of another various of an inductive tubing 172 according to the principles of the present invention. In this exemplary embodiment, inductive tubing 172 includes a first end 174, an opposite second end 176, a swivel component, such as example swivel connector 170 including a first end 178, an opposite second end 180 and a swivel member 182 therebetween, a first elongated tube 184 disposed between first end 174 of inductive tubing 172 and first end 178 of example swivel connector 170, and a second elongated tube 186 disposed between opposite second end 176 of inductive tubing 172 and opposite second end 180 of example swivel connector 170. Inductive tubing 172 includes a first inductive coil 188 wound about first end 174 of inductive tubing 172, a second inductive coil 190 wound about first elongated tube 184, a third inductive coil 192 wound about example swivel connector 170, a fourth inductive coil 194 wound about second elongated tube 186, and a fifth inductive coil 196 wound about opposite second end 176 of inductive tubing 172.

EXAMPLE 8

For example and without limitation, third inductive coil 192 can be an inductive coil 198 wound about first end 178 of example swivel connector 170 and another inductive coil 200 wound about opposite second end 180 of example swivel connector 170.

EXAMPLE 9

The present invention contemplated providing a swivel coupling between inductive tubing 172 and a patient interface device. The present invention further contemplates providing a swivel coupling between inductive tubing 172 and a pressure generating system. For example, a swiveling joint can relieve the torque between the mask and the blower. For this reason, inductive coupling techniques, as discussed above in connection with Examples 7 and 8, can also employed for such swivel connections. This enables swiveling of inductive tubing between a mask and a blower by a suitable swiveling joint to relieve torque between mask and blower.

EXAMPLE 10

In FIG. 6, third inductive coil 192 can include additional inductive elements (e.g., without limitation, inductive coils)

across swivel member 182 or a suitable slip joint (e.g., without limitation, a brush-type electrical connection) that electrically connects two separate inductive elements (e.g., without limitation, inductive coils, such as 198,200) on either side of swivel member 182.

EXAMPLE 11

Figure 7:
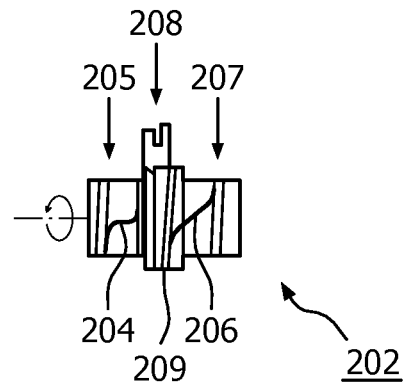
FIGS. 7 and 8 are elevation views of other swivel connectors in accordance with other embodiments of the invention.

Referring to FIG. 7, another swivel component, such as example swivel connector 202, is shown. In this example, third inductive coil 192 of Example 7 is a first inductive coil portion 204 wound about first end 205, a second inductive coil portion 206 wound about opposite second end 207, and an electrical slip joint 208 (e.g., without limitation, a brush-type electrical connection) electrically connecting first inductive coil portion 204 to second inductive coil portion 206, while permitting a swivel member 209 to suitably swivel.

EXAMPLE 12

Figure 8:
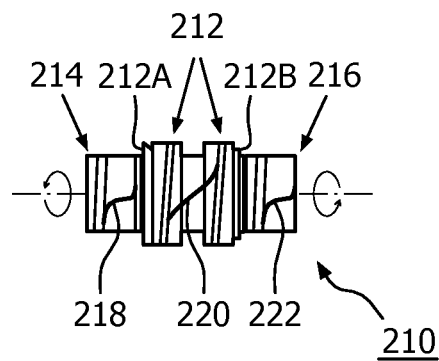

FIG. 8 shows another swivel component, such as example swivel connector 210. In this example, swivel connector 210 includes a plurality of swivel members 212 disposed between first end 214 and opposite second end 216. Third inductive coil 192 of Example 7 is a first inductive coil 218 wound about first end 214, at least one second inductive coil 220 wound between plurality of swivel members 212, and a third inductive coil 222 wound about opposite second end 216.

Here, for example, a plurality of swivels (e.g., without limitation, two swivels 212A,212B and three inductive coils 218,220,222) can be employed if the needs of the patient require additional freedom from torque in inductive tubing, such as 126,142,172.

EXAMPLE 13

Figure 9:
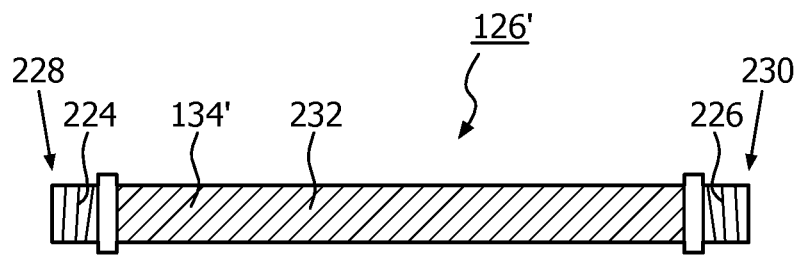
FIG. 9 is an elevation view of inductive tubing in accordance with another embodiment of the invention.

Referring to FIG. 9, inductive tubing 126' is somewhat similar to inductive tubing 126 of FIG. 4, which includes single inductive coil 134, as was described. In contrast, inductive tubing 126' includes two additional inductive coils 224, 226 at opposite ends 228,230, respectively. Inductive tubing 126' further includes an elongated tube 232 (e.g., without limitation, forming a ventilator tube) disposed between opposite ends 228,230 (e.g., without limitation, forming tubing connectors). Here, the number of inductive coils includes first inductive coil 224 wound about first end 228, second inductive coil 134' wound about elongated tube 232, and third inductive coil 226 wound about opposite second end 230.

Disclosed inductive tubing 126,142,172,126' allows a patient interface device, a tube and a blower to be easily coupled and decoupled. In this manner, such inductive tubing has enhanced capabilities inherent in its structure. For this reason, for the purpose of an air or gas conduit, it functions mechanically in precisely the same manner as a conventional tube not equipped with such inductive tubing. In addition, this provides a significant advantage over conventional heated tubes for continuous positive airway pressure (CPAP) therapy, which employ an electrical connector for direct electrical connection to a power source at a controller.

Furthermore, disclosed inductive tubing 126,142,172,126' can be suitably constructed (e.g., without limitation, using a suitable conductor gage; number of wraps or turns; overall conductor resistance over a tube length) to generate waste heat due to inefficiencies in such conductors. Consequently, inductive tubing 126,142,172,126' can also simultaneously or selectively heat the tube. This is an advantage since heated tubes give a better experience by delivering relatively warmer air or gas to the patient as well as air or gas that can hold relatively more moisture, since warmer air holds more moisture.

In addition, the reliability of the "connection" of disclosed inductive tubing 126,142,172,126', which does not require a direct electrical connection, is substantially higher than a conventional mechanical electrical connector that uses a direct electrical connection. This is because such mechanical electrical connectors are frequently viewed as being single-fault electrical connections since they can malfunction as a result of changes (e.g., without limitation, mechanical changes, such as contact bending and/or change in contact spring force; contact erosion; contact oxidation) to their structure. In other words, they wear out.

Disclosed inductive tubing 126,142,172,126' allows a number of input elements (i.e., sensors and/or controls) to be powered without a direct electrical connection, thereby enabling signal communication between such number of sensors and controls and a controlling unit, such as a CPAP blower. Such inductive tubing employs inductive coupling to transmit power and/or data between, for example, a pressure generating system and a number of sensors and controls of a patient interface device, such as a mask. This non-direct connectivity allows for reliable signal and power communication. In this manner, such inductive tubing can be employed to provide one or both of signal and power transmission. A conventional non-inductive tube can be substituted for such inductive tubing for lower cost or for situations demanding lower therapy capabilities. However, such conventional, non-inductive tube does not provide any enhanced capabilities, although the patient could still get CPAP therapy, but not with advanced functions enabled by such inductive tubing.

Although a CPAP support system is disclosed, any type of air or gas pressure support system (e.g., without limitation, medical therapy employing a breathing tube) can utilize disclosed inductive tubing 126,142,172,126' in, for example and without limitation, single-limb or two-limb (or dual-limb) systems.

Although the invention has been described in detail for the purpose of illustration based on what is currently considered to be the most practical and example embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support system comprising:
   (a) a gas flow generating system comprising:
      (1) a gas source,
      (2) a controller, and
      (3) a first inductive coil operatively coupled to the controller;
   (b) a patient interface device comprising:
      (1) an input element operatively coupled to the patient interface device, and
      (2) a second inductive coil operatively coupled to the input element and disposed on the patient interface device; and
   (c) a tubing disposed between the gas flow generating system controller and the patient interface device, the tubing being structured to carry a flow of air or gas from the gas source to the patient interface device, the tubing comprising a first end structured to couple with the gas source, a second end structured to couple with the controller, an elongated tube attached between the first end and the second end and having an elongated length between the gas flow generating system controller and the patient interface device, and a third inductive coil coupled to the elongated tube along the elongated length and wound about the first end, the second end, and the elongated tube, the tubing being structured to inductively couple power or a signal between the first inductive coil of the gas flow generating system controller and the second inductive coil of the patient interface device.

2. The pressure support system of claim 1, wherein input element is a sensor, wherein the patient interface device is a mask assembly including a frame and a cushion coupled to the frame, and wherein the sensor is coupled to the cushion or the frame and is in electrical communication with the second inductive coil.

3. The pressure support system of claim 2, wherein the sensor is structured to sense a physical phenomena selected from the group consisting of pressure, flow, temperature, vibration, g-force, electromyography (EMG), electroencephalography (EEG), electrocardiography (ECG or EKG), pH, sound and body position.

4. The pressure support system of claim 1, wherein the tubing further comprises a first end, an opposite second end and the elongated tube disposed between the first end and the opposite second end, and the third inductive coil is wound about the first end, the elongated tube, and the opposite second end.

5. The pressure support system of claim 1, wherein the gas flow generating system controller further comprises a processor including at least one power or communication component selected from the list consisting of a receiver, a transmitter, a transceiver and a power source, and wherein the at least one power or communication component is in electrical communication with the first inductive coil.

6. The pressure support system of claim 1, wherein the gas flow generating system controller further comprises a processor including a receiver and a power source, the receiver and the power source being in electrical communication with the first inductive coil, wherein the power source transmits power to the input element through inductive coupling between the first inductive coil and the third inductive coil, and between the third inductive coil and the second inductive coil, and wherein the input element transmits a signal to the receiver through inductive coupling between the second inductive coil and the third inductive coil, and between the third inductive coil and the first inductive coil.

7. The pressure support system of claim 1, wherein the gas flow generating system controller further comprises a processor including a transmitter in electrical communication with the first inductive coil, wherein the input element receives a control signal having one of a plurality of different states from the transmitter through inductive coupling between the first inductive coil and the third inductive coil, and between the third inductive coil and the second inductive coil, and wherein the input element is structured to respond differently to the different states of the control signal.

8. The pressure support system of claim 1, wherein the third inductive coil is structured to generate heat to warm a gas flow carried by the tubing.

9. The pressure support system of claim 1, wherein the tubing is a conduit having a wall, and wherein at least a portion of the third inductive coil is embedded in or adhered to the wall.

10. A pressure support system comprising:
(a) a gas flow generating system comprising:
    (1) a gas source,
    (2) a controller, and
    (3) a first inductive coil operatively coupled to the controller;
(b) a patient interface device comprising:
    (1) an input element operatively coupled to the patient interface device, and
    (2) a second inductive coil operatively coupled to the input element and disposed on the patient interface device; and
(c) a tubing disposed between the gas flow generating system controller and the patient interface device, the tubing being structured to carry a flow of air or gas from the gas source to the patient interface device, the tubing comprising an elongated tube having an elongated length between the gas flow generating system controller and the patient interface device, and a third inductive coil coupled to the elongated tube along the elongated length and structured to inductively couple power or a signal between the first inductive coil of the gas flow generating system controller and the second inductive coil of the patient interface device,
wherein the tubing further comprises a first end, an opposite second end and the elongated tube disposed between the first end and the opposite second end, and further comprising a fourth inductive coil wound about the first end, the third inductive coil wound about the elongated length of the elongated tube, and a fifth inductive coil wound about the second end; wherein the fourth inductive coil is not electrically connected to the third inductive coil; and wherein the third inductive coil is not electrically connected to the fifth inductive coil.

11. A pressure support system comprising:
(a) a gas flow generating system comprising:
    (1) a gas source,
    (2) a controller, and
    (3) a first inductive coil operatively coupled to the controller;
(b) a patient interface device comprising:
    (1) an input element operatively coupled to the patient interface device, and
    (2) a second inductive coil operatively coupled to the input element and disposed on the patient interface device; and
(c) a tubing disposed between the gas flow generating system controller and the patient interface device, the tubing being structured to carry a flow of air or gas from the gas source to the patient interface device, the tubing comprising an elongated tube having an elongated length between the gas flow generating system controller and the patient interface device, and a third inductive coil coupled to the elongated tube along the elongated length and structured to inductively couple power or a signal between the first inductive coil of the gas flow generating system controller and the second inductive coil of the patient interface device,
wherein the tubing further comprises a first end, an opposite second end, and further comprising a swivel component disposed between the first end and the second end, the swivel component including a first swivel end, an opposite second swivel end and a swivel member therebetween, wherein the elongated tube is a first elongated tube disposed between the first end and the first swivel end, and the tubing includes a second elongated tube disposed between the second end and the second swivel end, wherein the tubing further comprising a fourth inductive coil wound about the first end of the tubing, the third inductive coil wound about the first elongated tube, a fifth inductive coil wound about the swivel component, a sixth inductive coil wound about the second elongated tube, and a seventh inductive coil wound about the second end of the tubing, wherein the fourth inductive coil is not electrically connected to the third inductive coil, wherein the third inductive coil is not electrically connected to the fifth inductive coil, wherein the fifth inductive coil is not electrically connected to the sixth inductive coil, and wherein the sixth inductive coil is not electrically connected to the seventh inductive coil.

12. The pressure support system of claim 11, further comprising an eighth inductive coil wound about the first swivel end and a ninth inductive coil wound about the second swivel end.

13. The pressure support system of claim 11, wherein the fifth inductive coil is a first inductive coil portion wound about the first end of the swivel component, a second inductive coil portion wound about the opposite second end of the swivel component and an electrical slip joint electrically connecting the first inductive coil portion to the second inductive coil portion.

14. A method of providing a flow of gas to a patient comprising:
  employing a patient interface device comprising a first inductive coil and an input element;
  providing a gas flow from a gas flow generating system having a second inductive coil;
  communicating a flow of gas to the patient interface device from the gas flow generating system via a tubing comprising a first end structured to couple with the gas flow generating system, a second end structured to couple with the patient interface device, an elongated tube having an elongated length coupled between the patient interface device from the gas flow generating system, wherein the tubing includes a third inductive coil coupled to the elongated tube along the elongated length and wound about the first end, the second end, and the elongated tube; and
  transmitting power, a signal, or both between the input element and a controller in the gas flow generating system through inductive coupling between the first and the third inductive coils and between the second and the third inductive coils.

15. The method of claim 14, further comprising generating heat via the third inductive coil to warm the flow of gas carried in the tubing.

\* \* \* \* \*